United States Patent [19]

Akopov et al.

[11] 3,935,981

[45] Feb. 3, 1976

[54] SURGICAL APPARATUS FOR SUTURING ORGANS AND TISSUES WITH METAL STAPLES

[76] Inventors: Ernest Mikhailovich Akopov, Dubninskaya ulitsa, 61, kv. 88; Nikolai Nikolaevich Kapitanov, 8 ulitsa Oktyabrskogo polya, 5, kv. 9; Alexei Alexeevich Strekopytov, ulitsa Vsevoloda Vishnevskogo, 10, kv. 67; Evgenia Sergeevna Ogoltsova, Rogozhsky val, 13, korpus 3, kv. 14; Alexandr Ilich Paches, Ulitsa Medvedeva, 12/6, Kv. 5, all of Moscow, U.S.S.R.

[22] Filed: June 5, 1974

[21] Appl. No.: 476,559

[30] Foreign Application Priority Data
July 31, 1973  U.S.S.R............................. 1955101

[52] U.S. Cl. .................................................. 227/19
[51] Int. Cl.² .......................................... B25C 5/02
[58] Field of Search ........................................ 227/19

[56] References Cited
UNITED STATES PATENTS

| | | | |
|---|---|---|---|
| 2,344,071 | 3/1944 | Wilson et al. | 227/19 X |
| 3,017,637 | 1/1962 | Sampson | 227/19 X |
| 3,692,224 | 9/1972 | Astafiev et al. | 227/19 |

*Primary Examiner*—Granville Y. Custer, Jr.
*Attorney, Agent, or Firm*—Holman & Stern

[57] ABSTRACT

A surgical apparatus for suturing organs and tissues with metal staples, comprising a frame provided with an opening and a clamp member having, on a side facing the frame opening, a flat portion provided with recesses for bending staples, a staple head with a staple holder and a staple pusher, both mounted on the frame for perpendicular travel relative to the clamp member, as well as drives for the staple head and pusher. The clamp member is releasable connected to part of the frame, which permits tissues being sutured being brought to the holder from the flat portion side of said clamp member.

6 Claims, 8 Drawing Figures

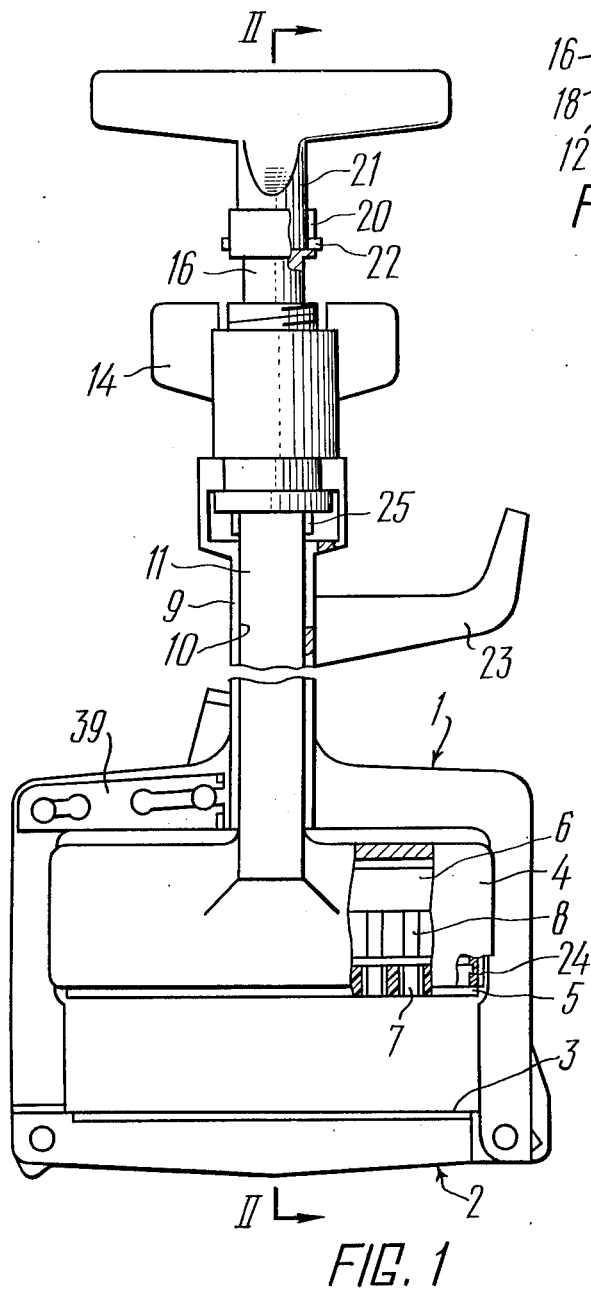
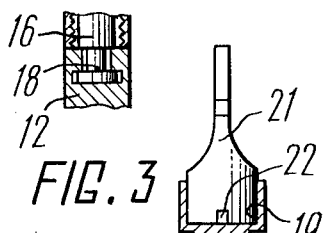
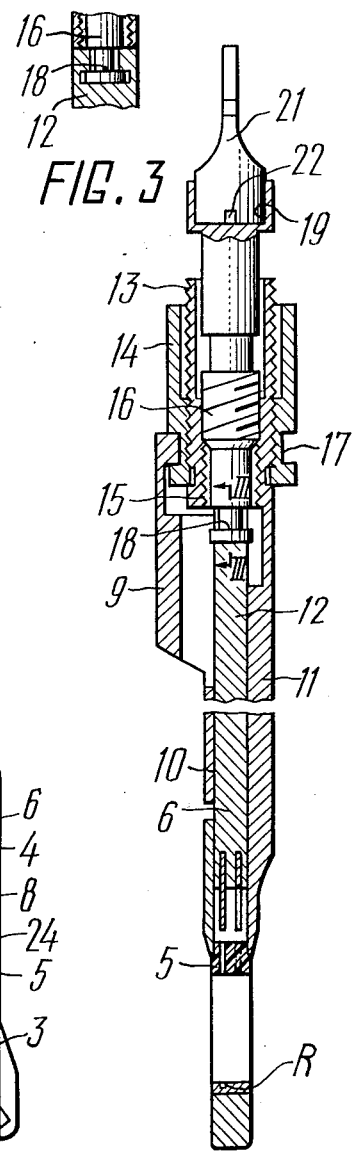
FIG. 1
FIG. 3
FIG. 2

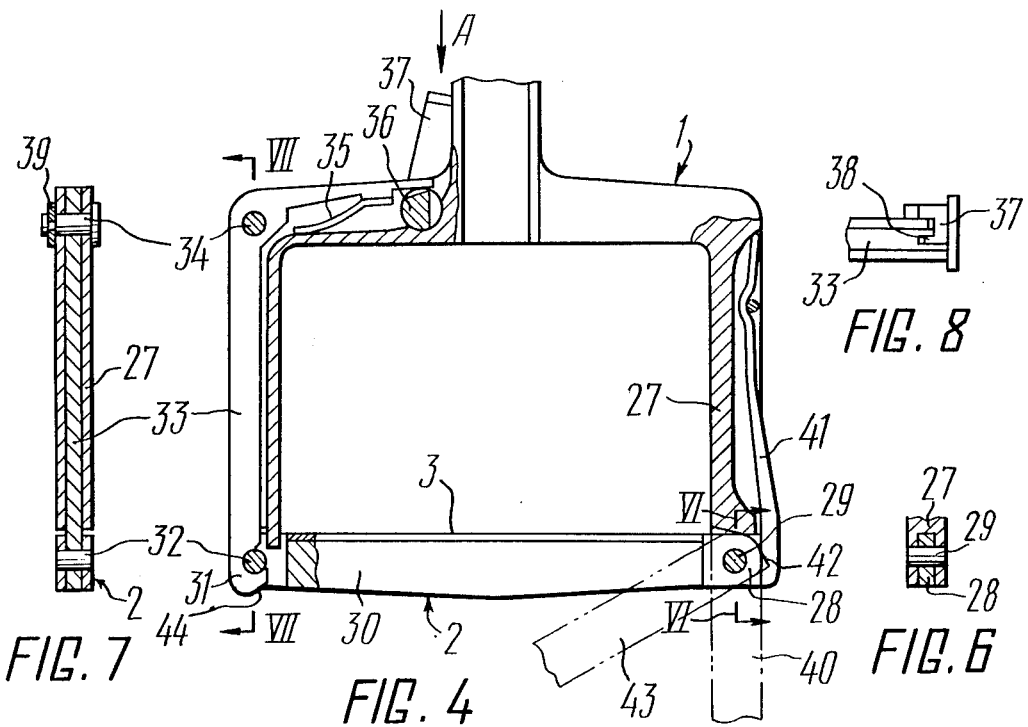

SURGICAL APPARATUS FOR SUTURING ORGANS AND TISSUES WITH METAL STAPLES

BACKGROUND OF THE INVENTION

The present invention relates to medical equipment and more particularly to surgical apparatus for suturing organs and tissues with metal staples. The proposed apparatus can find application in oncology for suturing the walls of the pharynx in laryngectomy in case of cancer as well as for suturing organs and tissues in the chest or abdominal cavity, e.g., the tissues of lungs, the stump of the stomach, intestines, and other organs.

Known in the art is a surgical apparatus for suturing organs and tissues with metal staples this known apparatus comprises a hook-shaped frame with a clamp member rigidly connected to the other part of the frame and having on the side facing the frame opening, a flat portion on which are recesses for bending the staple legs. Mounted in the frame for perpendicular travel relative to the above clamp member is a staple head provided with a holder for staples and with a staple pusher. Said staple head and pusher are provided with corresponding drives for their travel relative to the clamp member.

The holder has through slots for accommodation of metal staples therein. Said slots accurately match the recesses provided on the clamp member of the frame. The pusher has lugs corresponding to the holder slots. With the pusher moving toward the clamp member of the frame, the pushing lugs fit into the holder slots and push staples out of them.

Inserted in the staples head is an arresting fork for preventing a tissue or an organ being sutured from slipping out of the apparatus.

When applying the surgical apparatus, a tissue or an organ to be sutured should be between the flat portion of the clamp member and the operating face of the holder opposing said flat portion.

In such a position, the tissue or organ being sutured is inserted through the open lateral mouth of the hooked frame; then the tissue or organ is fixed by the arresting fork. The surgeon actuates the drive of the staple head bringing it closer to the clamp member so that a clearance necessary for suturing is set between the flat portion of the clamp member and the operating face of the holder. Thereafter the suturing of tissues is done by actuating the pusher drive; the lugs of the pusher pass through the holder slots and push the staples thereout; on puncturing the tissues being sutured, the staple legs strike against the recesses provided on the flat portion of the clamp member and are bent, thus suturing the tissues. The tissue portion to be disposed of is cut off, the holder is withdrawn from the clamp member, and the whole apparatus is removed from the operation incision.

A disadvantage of the known apparatus is its limited maneuverability that restricts its application for suturing in areas difficult of access, or for suturing under peculiar conditions when the space is limited for manipulations necessary to prepare the apparatus for the operation. This disadvantage is due to the design of the hooked frame shaped as a hook which permits the positioning of the holder and the clamp member of said frame to tissues being sutured only through the lateral opening of the frame. Whenever such positioning is not possible at all, or involves intolerable injury to the tissues being sutured or to the environmental tissues or organs because of shortage of space required for unimpeded manipulation with the apparatus in the operation cut, the use of the apparatus is actually impossible. Thus, in laryngectomy in cases of cancer with the aid of the known apparatus, the positioning of the clamp member of the frame and the holder under the tumor being operated on is possible only from the side of the chin or the chest which are distant from the suturing site. This is fraught with awkward and complicated manipulations in a limited space between the cutoff tumor and the remaining organs and tissues of the head and neck of a patient, which, moreover, result in tissue injury.

SUMMARY OF THE INVENTION

An object of the present invention is to provide a surgical apparatus for suturing organs and tissues with metal staples, the design of which would permit a traumatic positioning of the apparatus to tissues being sutured, as well as make it possible to suture not only organs of the chest and the abdominal cavity to which access is rather simple, but also organs and tissues which are difficult-of-access for the suturing operation; this extends the applications of this surgical apparatus.

The object of the invention is achieved in a surgical apparatus for suturing organs and tissues with metal staples, which comprises a frame with a clamp member being part of said frame and having, from the side of the frame opening, a flat portion made on which are recesses for bending the staple legs, a stapler head with a staple holder and a staple pusher fitted with corresponding drives and mounted on said frame for perpendicular travel relative to the flat portion of the clamp member, wherein, according to the invention, the clamp member is connected to the other part of the frame to facilitate the withdrawal of said clamp member so as to permit the positioning of tissues being sutured to the holder from the side of the clamp member.

It is expedient that the frame be made as a U-shaped brace with a clamp member attached to its ends, one end being hinged and the other being secured with a spring lock.

It is desirable that a spring lock be provided in the place where the clamp member is hinged to the U-shaped brace, as would hold the clamp member in a withdrawn position.

The spring lock may have a groove interacting with the end of the clamp member used to hold the clamp member in a partly withdrawn position.

The clamp member can be made as a U-shaped brace and secured on the other part of the frame, both of its ends being made disconnectable.

In this case, the clamp member can be held on the other part of the frame by means of channels provided on the ends of said member and inclined relative to the longitudinal axis of the frame as well as by means of joint pins secured on the frame to fit into these channels; moreover, the clamp member can be tightened by a spring available on the frame in a direction preventing the removal of the clamp member from said joint pins.

The proposed surgical apparatus features higher maneuverability and greater functional potentialities as compared with the known one, because it permits operations not only on organs of the chest or the abdominal cavity, but is found good for operations on other organs the access to which for suturing by known apparatuses is either difficult or practically impossible. Specifically, the proposed apparatus permits suturing of the walls of the pharynx in laryngectomy in case of cancer, the bringing of the clamp member of the frame, and the holder of the apparatus, to a suturing site being carried out laterally relative to the pharynx, which is much simpler and is not fraught with traumas to the pharynx and the remaining environmental tissues.

Unlike manual suturing of the pharynx walls employed presently in laryngectomy after cutting off the tumor being removed, the employment of the proposed apparatus helps to sharply reduce infection in the operation cut and in the pharynx by the content of the tumor being removed —as an initial operation involves suturing the pharynx walls, overlapping the opening of the portion being removed with the aid of a special clip, and subsequent cutting off of the tumor between the apparatus and a clip —improves the conditions for the regeneration of tissues, whose suturing is as a rule, effected after radiation therapy, and reduces appreciably the time required for suturing the pharynx and reduces post-operation effects.

The provision of the apparatus with a detachable clamp member according to the invention helps improve the maneuverability of the apparatus while its being brought to a suturing site in a tight and difficult-of-access cavity, because it permits initially placing of the detached clamp member under an organ being sutured and then attaching to said member to the other part of the apparatus, which is much bigger than the clamp member.

BRIEF DESCRIPTION OF THE DRAWINGS

The invention will become more apparent from the description of exemplary embodiments and drawings, wherein:

FIG. 1 shows schematically a surgical apparatus for suturing organs and tissues with metal staples, according to the invention, with portions broken away and sectional;

FIG. 2 is a section on line II—II in FIG. 1;

FIG. 3 is an enlarged section on line III—III in FIG. 2;

FIG. 4 is a fragmentary elevation of the frame with a clamp member, according to the invention;

FIG. 5 is another embodiment of the frame with a clamp member, according to the invention;

FIG. 6 is a section on line VI—VI in FIG. 4;

FIG. 7 is a section on line VII—VII in FIG. 4;

FIG. 8 shows a detail taken, on arrow A in FIG. 4;

FIG. 9 is a section on line IX—IX in FIG. 5.

DESCRIPTION OF THE PREFERRED EMBODIMENT

The surgical apparatus for suturing tissues with staples comprises a frame 1 (FIG. 1) provided with a clamp member 2 having an opening bracketed by a pair of parts, and , from the side of the opening of the frame 1, a flat portion 3 made on which are recesses R for bending the staple legs; see FIG. 2. Attached to the frame 1 is a staple head 4, and a holder 5 and a pusher 6 are inserted into head 4. The holder 5 has through slots 7 for the accommodation of staples therein and the pusher 6 has lugs 8 intended for pushing staples from said holder 5. The craters of the member 2, the slots 7 of the holder 5, and the lugs 8 of the pusher 6 are arranged to correspond to each other.

Coupled with the frame 1 is a stem 9 provided with a groove 10 arranged perpendicular to the flat portion 3 of the clamp member 2 of the frame 1. The staple head 4 has a rod 11, while the pusher 6 has a rod 12 (FIG. 2) provided in the groove 10 of the stem 9 of the frame 1. The rod 11 is made to have an exterior thread 13 at its end in order to accept a nut 14, and is provided with a threaded hole 15 inserted into which is a screw 16. The nut 14 is a drive of the staple head 4 and has a circular groove 17 for interacting with the stem 9 of the frame 1. The screw 16 is a drive for the pusher 6 and has a circular groove 18 (FIGS. 2 and 3) at one of its ends, coupled with which is a fork at the end of the rod 12 of the pusher 6 (FIG. 2), while the other end has a hole 19 with grooves 20 (FIG. 1) inserted into which is a detachable handle 21 of the drive of the pusher 6 with lugs 22 for interaction with the grooves 20. Connected rigidly with the stem 9 of the frame 1 is a handle 23 for holding the apparatus. The staple head 4 has lateral grooves 24 which interact, as said head 4 moves relative to the clamp member 2, with the lateral sides of the frame 1. The rod 11 of the staple head 4 is made to have lugs 25 for interacting with the corresponding grooves of the stem 9 of the frame 1.

The drawings of the invention show two exemplary embodiments of the frame 1 (FIGS. 4 and 5). In both embodiments, the frame 1 is made closed, but, in principle, it can be made not closed too, as, e.g., in the form of a hook. What is important is that the clamp member 2 (FIG. 4) or 26 (FIG. 5) should be linked with the other portion of the frame. Further, member 2 should have the capability of being withdrawn from the other frame portion so as to permit the holder 5 an access to tissues from the side of the clamp member 26 or 2 (FIG. 4).

In the first embodiment, shown in FIG. 4, the frame 1 is made as a U-shaped brace 27 secured to whose ends is a clamp member 2 in the form of a pivotal plate. One end 28 of the clamp member 2 is connected to the brace 27 by means of a hinge 29 (FIGS. 4 and 6), while the other end 30 (FIG. 4) is connected to the same brace by means of a lock 31 which grips a pin 32 (FIGS. 4 and 7) on the clamp member 2. Said lock 31 (FIG. 4) is arranged on a rocking bar 33 coupled with the brace 27 of the frame 1 by means of an axle 34, and is pressed against the pin 32 by a spring 35 secured on the rocking bar 33 and fixed in that position by means of a turnable cam 36 provided with a lever 37. The lever 37 has a lug 38 (FIG. 8) adapted to act on the rocking bar 33 (FIG. 4) when the lever 37 turns toward the frame 1, this is necessary for disengaging the lock 31 from the pin 32 of the clamp member 2. The axle 34 and the cam 36 are secured on the brace 27 with the aid of a detachable plate 39 (FIGS. 1 and 7).

Depending on the anatomic and topographic position of an organ being sutured and on an access to it, the clamp member 2 is expediently placed in a different initial position with respect to the brace 27 (FIG. 4) of the frame 1.

In the initial position, when the apparatus is brought to a portion being sutured, the clamp member 2 is withdrawn and set in a position 40, being an extension of the lateral side of the brace 27 of the frame 1. In such withdrawn position 40, the clamp member 2 is locked by a spring lock 41 secured by one of its ends onto the lateral side of the brace 27. The lock 41 is made with a groove 42 which interacts with the end 28 of the clamp member 2 and locks it in a position 43 at an angle 25°–40° to its working position. Thanks to the fact that the clamp member 2 is able to be set in the partly withdrawn position 43, convenient use is made for the apparatus to suture organs and tissues of the chest and the abdominal cavity being in the depth of an operating wound. When the clamp member 2 is set in its working position, the pin 32 acts on an inclined surface 44 of the lock 31.

In the second embodiment, the clamp member 26 (FIG. 5) of the frame 1 is made as a detachable part whose ends are releasably to the other part of the frame 1. The clamp member 26 in the embodiment shown in FIG. 5 is an U-shaped brace whose lateral sides have on their ends closed type slots 45 inclined relative to the longitudinal axle of the frame 1 for connection with pins 46 (FIGS. 5 and 9) rigidly coupled with the other part of the frame 1.

The frame 1 (FIG. 5) is equipped with a spring 47 designed to press the walls of the slots 45 to the pins 46 and ensure the easy and dependable connection of the clamp member 26 with the rest of the frame 1.

The surgical apparatus with the clamp member 2 (FIG. 4) made as a folding-back plate operates in the following way:

For setting clamp member 2 into its initial position, it is necessary to press the lever 37 of the cam 36 against the frame 1. This is accomplished by pressing on the rocking bar 33; bar 33 thus turns to disengage the lock 31 from the pin 32 of the clamp member 2; taking the end 30 of said clamp member 2 it is necessary to turn it until it stops in a position 40. In this position 40, the clamp member lies along the lateral side of the U-shaped brace 27 of the frame 1.

Then, for suturing, for instance, the walls of the pharynx, it is necessary to draw up the larynx prepared for a surgical removal as much as possible and to bring the apparatus from the side under the larynx (perpendicular to the mouth axis) so that the lateral sides of the opened frame 1 should pass under the dissected tissues near the tongue root and envelop the larynx portion being sutured from the side of the chest and the chin.

For connecting the clamp member 2 with the lock 31, it is necessary to turn the clamp member 2 around the hinge 29 until it rests against the frame 1, the lock 31 gripping, under the action of the spring 35 of the rocking bar 33, the pin 32 of said member 2. By reversely turning the lever 37 up to the stop, the cam 36 is made to fix the bar 33 and the clamp member 2 in the operating position.

By turning the nut 14 (FIG. 1) of the staple head 4, the tissues between the clamp member 2 and the holdeer 5 are pressed and a suturing clearance is set, while the rotation of the handle 21 of the screw 16 of the pusher 6 results in pushing staples out of the holder 5 and suturing.

A special clamp is put on the portion of the pharynx walls being removed for overlapping the opening of this portion and preventing the operation cut from infection, and the tissues between said clamp and the apparatus are dissected with scalpel thereafter. Once the portion of the pharynx and the larynx is removed, the holder 5 is brought away from the clamp member 2 by turning the nut 14 of the staple head 4 in an opposite direction and the apparatus is withdrawn from the operation cut.

If it is necessary to place the clamp member 2 in an intermediate position 43 (FIG. 4) for bringing it under the organ being sutured, which may be deep in the operation cut in the chest or abdominal cavity. The clamp member 2 should be turned, prior to the apparatus application, unless the end 28 of the clamp member 2 is locked by means of the groove 42 of the spring lock 41. The rest of the apparatus operations correspond to the phases considered for the case of the apparatus application for suturing the pharynx.

The apparatus with a detachable clamp member 26 (FIG. 5) operates in the following way.

By pressing on the clamp member 26 in the direction of a spring 47, the slots 45 are brought out of engagement with the pins 46 and the clamp member 26 is disconnected from the other part of the frame 1. Then said clamp member 26 is brought to a suturing site.

To arrange the tissues being sutured between the clamp member 26 and the holder, said clamp member 26 should be connected with the other part of the frame 1 by inserting pins 46 into closed-type sloped slots 45.

In doing so, one of the lateral sides of the brace of the clamp member 26 should be arranged between the spring 47 and the pin 46 and both of the sides of the brace should be pressed against the other part of the frame 1. Upon releasing the clamp member 26, the spring 47 biases the member 26 onto the pins 46 of the frame 1. Thereafter the operation according to the second variant does not differ from the operation of the apparatus fitted with the clamp member 2 (FIG. 4) made as the folding back plate.

What we claim is:

1. A surgical apparatus for suturing organs and tissues with metal staples, comprising, in combination:
   a. a frame having an opening and including a pair of parts;
   b. a clamp member mounted on one of the parts of said frame and releasably connected to the other part of the frame for permitting a free insertion of the organ being sutured into said opening of the frame after the clamp member has been displaced relative to the other part of the frame;
   c. said clamp member including a flat portion having recess means for bending legs of staples;
   d. a staple head mounted on the frame and including means for guiding the staple head in a path of perpendicular travel relative to said flat portion of the clamp member;
   e. a drive connected to said staple head for causing its travel;
   f. a holder on said frame spaced from said clamp member for metal staples inserted into the staple head, whereby tissues being sutured can be arranged between the clamp member and the holder;
   g. a pusher for staples mounted on said frame for perpendicular travel relative to said clamp member for pushing staples from the holder, through the tissues and into engagement with the recess means of the flat portion of the clamp member; and
   h. a drive on the frame connected to said pusher for operating the pusher in relation to the clamping member.

2. A surgical apparatus as in claim 1, wherein said frame comprises a U-shaped member having a pair of ends, said clamp member having a pair of ends, one end hinged to one of the ends of said U-shaped member and the other end of said clamp member being releasably connected to the other of the ends of said U-shaped member by means of a spring lock.

3. A surgical apparatus as set forth in claim 2, including a second spring lock engagable with said clamp member adjacent the hinge and including means for retaining the clamp member in different angular positions of adjustment.

4. A surgical apparatus as set forth in claim 3, wherein said second spring lock comprises a groove in which said clamp member is pivoted, and a resilient element engagable on said clamp member for retaining it in its different angularly adjusted positions.

5. A surgical apparatus as in claim 1, in which said clamp member is provided with slots on its ends which are inclined relative to the longitudinal axis of said frame; pins provided on said frame and fitted into said slots of the clamp member; and a spring secured on said frame and acting on said clamp member so as to prevent the removal of said clamp member from said slots.

6. A surgical apparatus as set forth in claim 1, wherein said frame is U-shaped, and said frame and clamp member include cooperating connecting means at both ends of the clamp member whereby said clamp member can be removed in its entirety from said frame.

* * * * *